United States Patent [19]

Kurth

[11] Patent Number: 4,829,994

[45] Date of Patent: May 16, 1989

[54] FEMORAL COMPRESSION DEVICE FOR POST-CATHETERIZATION HEMOSTASIS

[76] Inventor: Paul A. Kurth, 1423 Brett Pl., Apt. 201, San Pedro, Calif. 90732

[21] Appl. No.: 54,751

[22] Filed: May 27, 1987

[51] Int. Cl.$^4$ ................................................. A61F 5/24
[52] U.S. Cl. ................................. 128/96.1; 128/107.1; 128/327; 128/DIG. 15
[58] Field of Search .................... 128/95.1, 96.1, 98.1, 128/99.1, 100.1, 101.1, 106.1, 107.1, 327

[56] References Cited

U.S. PATENT DOCUMENTS

| | | | |
|---|---|---|---|
| 174,450 | 3/1876 | Werum | 128/112.1 |
| 1,916,298 | 4/1933 | Brohman | 128/96.1 |
| 2,449,641 | 9/1948 | Cidissen | 128/96.1 |
| 2,475,488 | 7/1949 | Fine | 128/101 |
| 2,522,056 | 9/1950 | O'Brien | 128/96.1 |
| 2,606,551 | 8/1952 | Piper | 128/96.1 |
| 3,021,838 | 2/1962 | Fine | 128/96.1 |
| 3,097,641 | 7/1963 | Nelkin | 128/96.1 |
| 3,247,842 | 4/1966 | Spasic | 128/95.1 |
| 3,308,813 | 3/1967 | Loeffel | 128/96.1 |
| 3,399,675 | 7/1968 | Trznadel et al. | 128/101 |
| 3,577,986 | 5/1971 | Regent | 128/96 |
| 3,625,219 | 12/1971 | Abrams et al. | 128/325 |
| 3,754,549 | 8/1973 | Nelkin | 128/100.1 |
| 3,799,249 | 12/1973 | Semler | 128/325 |
| 4,182,338 | 1/1980 | Stanulis | 128/325 |
| 4,233,980 | 11/1980 | McRae et al. | 128/325 |
| 4,351,325 | 9/1982 | Walker | 128/96.1 |
| 4,416,272 | 11/1983 | Nelkin | 128/95.1 |
| 4,427,007 | 1/1984 | Rexroth | 128/325 |
| 4,576,154 | 3/1986 | Hyman et al. | 128/78 |

FOREIGN PATENT DOCUMENTS 1388168 12/1964 France .

Primary Examiner—Robert A. Hafer
Assistant Examiner—Kevin G. Rooney
Attorney, Agent, or Firm—Beehler, Pavitt, Siegemund, Jagger, Martella & Dawes

[57] ABSTRACT

An improved femoral aterial or venous compressive device is comprised of a flexible pelvic apron positioned over the femoral vessels within the human pelvis. The pelvic apron is placed in position by means of a hip strap. The hip straps are led from the pelvic apron upwardly over the hip points, around the small of the back and down over the opposing hip point back to the pelvic apron. The pelvic apron thus hangs from the hip points of the pelvis much like an apron. A shaped mass or pellet is attached to the under side of the pelvic apron over the incision site of the femoral vessel. An elastically extensible groin strap is then attached to the pelvic apron in the proximity of the shaped mass and drawn tightly through the groin, around the back of the leg, under the buttocks and back upwardly to the pelvic apron in the proximity of the shaped mass. As a result, the tensile force is applied by the groin strap across the pelvic apron up to the hip point and also around the leg. The shaped mass is forced by the tourniquet action of the groin strap and pelvic apron in combination downwardly into the pelvis, thereby compressing the underlying femoral vessel and thus assising in stanching any blood flow or fluid leakage.

16 Claims, 3 Drawing Sheets

FEMORAL COMPRESSION DEVICE FOR POST-CATHETERIZATION HEMOSTASIS

BACKGROUND OF THE INVENTION

1. Field of the Invention

The invention relates to the field of medical sciences and in particular to devices used to facilitate femoral vascular stanching.

2. Description of The Prior Art

During cardiac catheterization and angiography, it is necessary to obtain access to the heart and other major body arteries and veins in order to visualize them with radioopaque materials. One of of the preferred sites for such major vascular access is through the major femoral arteries and veins in the groin. The typical prior art procedure is to insert appropriate tubing into the femoral vessels through a small incision in the groin. The tube is later removed leaving a perforation in the femoral artery and/or vein. Normal blood clotting is utilized to render the repaired incision and vascular perforation blood-tight. Manual pressure is applied to the incision site for at least twenty minutes following removal of the tube from the artery or vein to allow for a clot of strength sufficient to withstand the arterial pressure of 120-180 mm Hg. Normally, manual pressure by trained medical personnel is sufficient to successfully clot the femoral arterial or venous perforation site and stanch the blood flow. However, despite this twenty minute time period the clot is soft and can be easily disrupted. Therefore, for some period of time thereafter it is advantageous to maintain a compressive force on the femoral puncture site to insure that it remains stanched.

The typical prior art procedure is to manufacture a thick pad of gauze which is placed over the site and taped securely to the patient's hip and groin in order to secure it in place and to maintain some compressive force over the incision site. The compressive force is generated and maintained by virtue of the bulk of the folded gauze pad pressed downwardly by the adhesive tape which is laid over the pad and which is attached on either side of the incision site to adjacent portions of the hip and groin.

Pursuant to the normal usage of such gauze and adhesive tape bandages, all contiguous areas of the incision site must be shaved and coated with an antiseptic and/or skin toughening agent. Approximately twenty-four hours later the bandages can be removed. However, a considerable amount of the body area in the area of the hip and groin is taped so that removal of the bandages is often an unpleasant and uncomfortable experience for the patient. Often some abrasion or skin tearing results and at the very least, there is some infliction of sharp temporary pain since the body area has been traumatized and is tender. Further, in many cases, patients may develop an allergic reaction to the adhesive or antiseptic applied to the body causing further tenderness and pain upon removal of the tape.

Further, if in the event that movement by the patient causes the blood clot to be damaged or dislodged, it may be necessary to reapply manual pressure and apply a new compression pad to the patient. In such a case, the old bandage must be quickly removed and the new bandage applied with the result that the patient may be subjected to the pain and discomfort of bandaging and unbandaging several times during the initial convalescence.

To avoid each of these drawbacks, the prior art has devised a groin compression device known as the Colapinto compression device, named after its creator in Canada. The Colapinto compression device is manufactured and sold under that name by Cook of Bloomington, Indiana.

FIG. 1 is a frontal view of a patient bearing the prior art Colapinto device, generally denoted by reference numeral 10. FIG. 2 is a side view of the patient wearing the Colapinto device of FIG. 1. Briefly, the Colapinto device 10 includes a groin pad 12 which has a bi-lobed shape. A waist strap 14 is sewn at end 16 to groin pad 12 and wraps around the lower hips below the hip points, across the upper part of the buttocks and around the buttocks to the other side of groin pad 12 where strap 14 is attached at end 18 by means of a Velcro attachment provided to end 18 of strap 14 and the corresponding proximate portion of groin pad 12. Sewn to the lower center portion of groin pad 12 are two stabilizing straps 20 which are drawn between the legs and around the lower portion of each buttock and attached at end 22 to a Velcro fastener on strap 14 to the middle of the side of the hip as depicted in FIG. 2 below the hip point. The purpose and function of straps 20 are to provide only stabilization to groin pad 12 and they do not add in any material way to the compressive force applied by groin pad 12 to the underlying femoral arterial or venous incision site.

Shown in dotted outline in the left groin region under groin pad 12 in FIG. 1 is a styrofoam pellet in the shape of a sector of a sphere with a flattened pole. The diameter or cord of the sector is approximately $2\frac{7}{8}''$ with the thickness of the pellet from the flattened pole face to the base defined by the section is approximately one inch. Pellet 24 therefore is roughly hemispherical with a flattened pole face of approximately an inch across and serves to replace the equivalent amount of folded gauze to define the pressure point against the femoral arterial or venous incision.

Two material characteristics of the Colapinto compression device should be immediately noted. Firstly, the compressive force applied to pellet 24 by device 10 is substantially if not entirely created by virtue of the tension of waist strap 14. Pellet 24 is disposed on the relatively flattened front portion of the groin and the amount of downward compressive force which can be developed on pellet 24 by virtue of the tension of waist strap 14 is significantly limited.

Secondly, the Colapinto compression device can be used only either on the left or on the right femoral arterial site. For example, in the depiction of FIG. 1, if application to the left femoral arterial site was desired, pellet 24, which is attached by means of a Velcro fastening device to the back of groin pad 12, can be shifted to the left side of groin pad 12 and the entire groin pad similarly shifted to the left to position pellet 24 over the arterial site. The size and extent of groin pad 12 of the Colapinto device is not sufficient to allow simultaneous application to both left and right femoral arterial sites. In any case, it is unlikely that sufficient compressive force could be developed if two pellets were positioned underneath groin pad 12.

Therefore, what is needed is a compression device which overcomes each of the defects of the prior art and in particular which can apply a large and adjustable compression force to either the left or the right femoral vascular sites, or to both.

BRIEF SUMMARY OF THE INVENTION

The invention is an apparatus for applying pressure to a femoral artery or vein within a human body comprising a pellet for applying a directed force to the human body, a pelvic apron and a groin strap. The pelvic apron positions the pellet over the femoral vessels. The groin strap applies a compressive force to the pellet which tends to compress the femoral artery and vein, so that a substantial force is adjustably applied to the femoral artery and blood flow therefrom is stanched.

The pelvic apron comprises a flexible pelvic apron piece and a flexible hip strap having two ends. Each end is attached to the pelvic apron piece. The hip strap positions the pelvic apron piece on the human body.

The human body is characterized by having hip points defined by pelvic bones and the hip strap extends from the pelvic apron over the hip points.

The flexible pelvic apron piece is substantially non-extensible and the hip strap is elastically extensible.

The groin strap is an elastically extensible strap having two ends. One end of the groin strap is attached to the pelvic apron piece in the proximity of the pellet. The groin strap is led through the groin of the human body around the corresponding leg and attached to the pelvic apron piece in the proximity of the pellet.

The groin strap is temporarily attached at one end to the pelvic apron piece and temporarily attached at the opposing end of the groin strap to the first end of the groin strap attached to the pelvic apron piece. Attachment of the groin strap to the pelvic apron piece and to its own end is in the proximity of the pellet assembly.

The pelvic apron piece is comprised of a basal portion and at least one inclined portion. The inclined portion has a linear extent lying in a predetermined direction when the pelvic apron piece is disposed on the human body. The predetermined direction is directed to the hip point. The hip strap extends in a colinear direction with the predetermined direction to wrap around the hip point. The hip strap continues across the back of the human body and over the opposing hip point to be reattached to the pelvic apron piece. The groin strap is attached to the pelvic apron piece and lies in a colinear direction with the predetermined direction.

The groin strap is adjustable to provide variable tension along the groin strap and thus downward compression of the pellet assembly toward the femoral artery and vein.

In one embodiment, two pellets are used and attached to the pelvic apron piece. Each pellet is shaped to transmit force applied to the pellet to a predetermined area of the human body in contact with the pellet.

The invention is also characterized as a compression device for use as a femoral arterial or venous clotting apparatus for application to a human pelvis which includes a pair of opposing hip points, a groin, corresponding legs and corresponding femoral arteries and veins extending through the pelvis into each of the legs. The device comprises a shaped mass having a first and second surface. A force applied to the first surface is transmitted through the mass to the second surface. The second surface is arranged and configured for placement against the pelvis in the proximity of the femoral artery and vein to apply compressive force when the mass is urged into the pelvis against the femoral vessels. A pelvic apron piece securely positions the shaped mass on the human pelvis. The shaped mass is attachable to the pelvic apron piece at a predetermined range of locations between the pelvic apron piece assembly and the human pelvis. The pelvis apron piece covers at least a frontal portion of the human pelvis. A groin strap is adjustably coupled to the pelvic apron piece for urging the shaped mass downwardly into the human pelvis. As a result, the shaped mass is positioned by the pelvic apron piece, and the compressive force is transmitted to the first surface of the shaped mass by combination of tension applied by the groin strap assembly to the pelvic apron piece assembly.

The pelvic apron piece is positionally fixed with respect to one of the hip points and the groin strap applies a tensile force across the pelvic apron piece to the hip point and through the groin wherein an inwardly compressive force is applied to the first surface of the shaped mass.

The groin strap is elastically extensible and tensile force is applied by the elastically extensible groin strap assembly is variably adjustable.

The pelvic apron piece is comprised of a substantially non-extensible pelvic apron piece and an elastically extensible hip strap for binding the pelvic apron piece to the hip points of the pelvis.

The groin strap has two ends. A first end is connected to the pelvic apron piece. The groin strap is led through the groin around the corresponding leg and the second opposing end of the groin strap is attached to the pelvic apron piece.

The two ends of the groin strap are each connected to the pelvic apron piece in the proximity of the shaped mass.

The invention is still further characterized as a method for applying a compressive force to a femoral artery or vein within a human pelvis. The pelvis has two opposing hip points and a groin. The method comprises the steps of stabilizing a shaped mass in position over a selected one of the femoral arteries or veins in the human pelvis. The shaped mass is stabilized relative to at least one of the hip points. The method continues with the step of applying a downward tensile force through the groin on a pelvic apron piece coupled to the shaped mass. The tensile force is directed through the groin to the rearward portion of the human pelvis substantially pivoted about the hip point so that a downward compressing force is applied to the shaped mass and ultimately against the underlying femoral vessels.

In the step of stabilizing the shaped mass in position, the shaped mass is positioned over the femoral artery and vein by attachment to a pelvic apron piece. The pelvic apron piece is positioned in turn over the human pelvis by means of a hip strap. The hip strap encircles the human pelvis and lying over the opposing points.

In the step of applying the tensile force to the pelvic apron piece, the tensile force is applied to the pelvic apron piece by means of an extensible elastic groin strap attached at one end to the pelvic apron piece, which is led through the groin, behind the corresponding leg and is attached at its opposing end to the pelvic apron piece in the proximity of the shaped mass.

The invention and its various embodiments are better visualized by now turning to the following drawings wherein like elements are referenced by like numerals.

The invention and its various embodiments may be better understood by now turning to the following detailed description.

DETAILED DESCRIPTION OF THE PREFERRED EMBODIMENTS

An improved femoral arterial and venous compressive device is comprised of a flexible pelvic apron positioned over the femoral arteries and veins within the human pelvis. The pelvic apron is placed in position by means of a hip strap. The hip straps are led from the pelvic apron upwardly over the hip points, around the small of the back and down over the opposing hip point back to the pelvic apron. The pelvic apron thus hangs from the hip points of the pelvis much like an apron. A shaped mass or pellet is attached to the under side of the pelvic apron over the puncture or incision site of the femoral vessels. An elastically extensible groin strap is then attached to the pelvic apron in the proximity of the shaped mass and drawn tightly through the groin, around the back of the leg, under the buttocks and back upwardly to the pelvic apron in the proximity of the shaped mass. As a result, the tensile force is applied by the groin strap across the pelvic apron up to the hip point and also around the leg. The shaped mass is forced by the tourniquet action of the groin strap and pelvic apron in combination downwardly into the pelvis, thereby compressing the underlying femoral artery and vein, and thus assisting in stanching any blood flow or fluid leakage.

Figure 3:
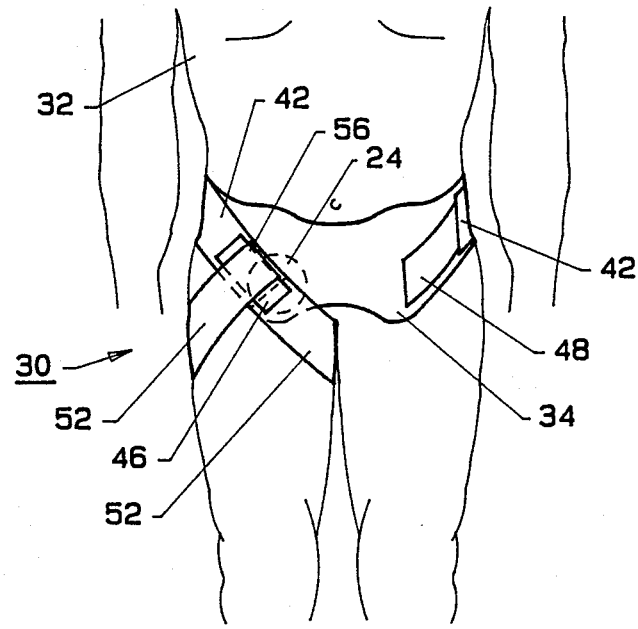
FIG. 3 is a front plan view of a compression device devised according to the invention.

The compression device of the invention, generally denoted by reference numeral 30, is depicted in the elevational plan view of FIG. 3 as fitted to a patient 32. The compression device 30, also to be known as the Kurth compression device, is comprised of a pelvic apron 34 made of a rubberized or substantially nonextensible fabric. As better depicted in plan view in FIG. 6, where Kurth compression device 30 is laid out flatly, pelvic apron 34 has a generally flattened V-shape comprised of a right upwardly extending leg 36, a bottom and mid-section 38 and a correspondingly left upwardly extending leg 40.

Figure 4:
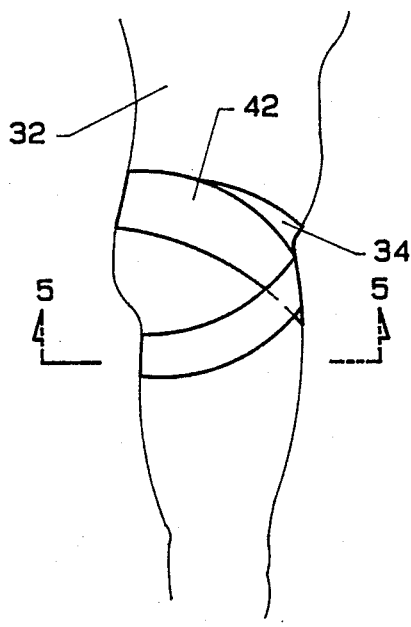
FIG. 4 is a side view of the compression device as applied to the patient as seen in FIG. 3.

Pelvic apron 34 of the Kurth compression device 30 differs from the Colapinto groin pad 12 in at least two significant respects. Firstly, pelvic apron 34 of Kurth compression device 30 is broader and spans the entire frontal pelvic region of patient 32. Thus, pelvic apron 34 is of sufficient size and extent such that a pellet, such as pellet 24 shown in FIG. 1, and shown in dotted outline in FIG. 3 and in a bottom perspective view in FIG. 6, can be placed over either the left or right femoral site or both without shifting the position of pelvic apron 34 on patient 32. Secondly, upwardly extending portions 36 and 40 of pelvic apron 34 extend at a sharper angle to the horizontal than do the corresponding portions of the Colapinto device of FIG. 1 and 2. As seen in FIGS. 3 and 4, the angle of pelvic apron 34 is such that elastic strap 42 which lies along the line or direction of portion 40, for example, extends upwardly at an angle so that strap 42 lies directly over the patient's hip points or pelvic hip bones.

Figure 6:
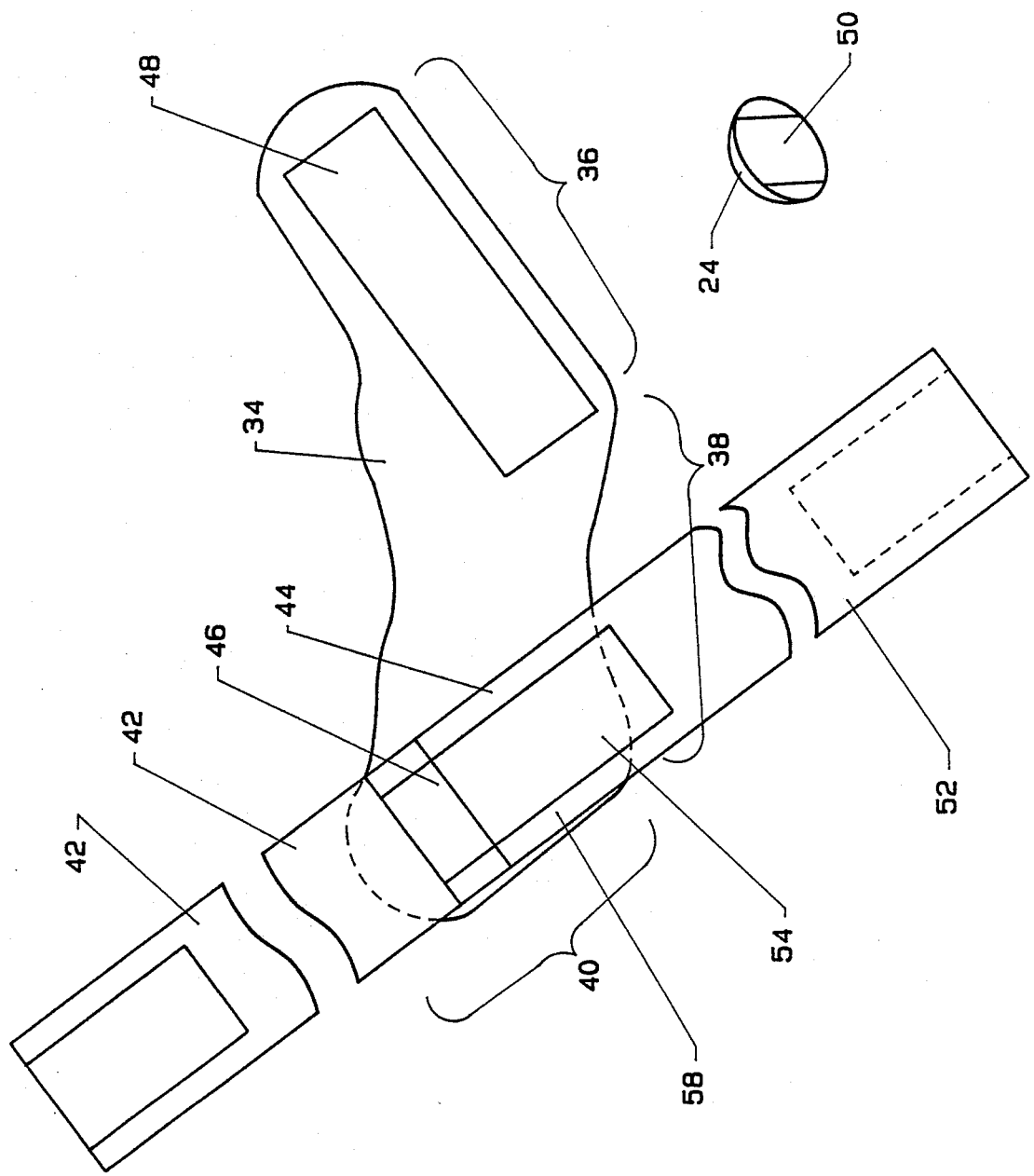
FIG. 6 is a front plan view of the compression device shown in broken away plan view as would be seen if the device were laid out flat.

As best depicted in FIG. 6, strap 42 is an elastic strap approximately three inches across as opposed to the Colapinto device which uses a two-inch strap. Strap 42 is sewn at one end to pelvic apron 34 and has a Velcro fastening patch 46 sewn to its outer surface overlying portion 40 of hip plate 34. A similar Velcro patch 48 is sewn to the opposing portion 36. In the illustrated embodiment, Velcro patches 46 and 48 act as hard hooks which are arranged and configured to engage a corresponding felt patch which acts as eyes of the Velcro fastener.

As shown in side view in FIG. 4, strap 42 is drawn upwardly over the hip bone and across the lower back of patient 32 and attaches to the upper portion of Velcro patch 48 as depicted in FIG. 3. Thus, on the inside surface of strap 42 is a soft felt Velcro strip of eyes (not shown) which can be placed against the hard Velcro hooks on patch 48. The angle of strap 42 as it attaches to patch 48 is generally parallel to the angle of portion 36 of pelvic apron 34 and also rides over the adjacent hip point.

Pellet 24, which is shown in the illustrated embodiment of FIG. 3, is attached to pelvic apron 34 over the right femoral vascular site and prior to the attachment of groin elastic strap 52 has at this time very little compressive force applied to it. Pellet 34 is maintained in place and connected to the under side of pelvic apron 34 by a Velcro attachment which is sewn to the appropriate position on the under side of pelvic apron 34 (not shown). An opposing and corresponding Velcro attachment patch 50 is glued or otherwise attached to the bottom of plastic or styrofoam pellet 34 as shown in perspective view in FIG. 6. Because of the spatial extent of both patch 50, pellet 24 and the corresponding patch on the bottom side of pelvic apron 34, the exact position of pellet 24 can be varied with a fair degree of latitude to position it directly over the incision site.

In any case, after pelvic apron 34 has been secured to the patient by means of hip strap 42, it is positioned on the under side of pelvic apron 34, which at this point would essentially hang loosely downward if the patient were to stand.

The Kurth compression device 30 further comprises a separate compression strap 52 which is an identical elastic strap approximately 22 inches long, as depicted in broken plan view in FIG. 6. Groin strap 52 is provided with a Velcro patch on its under side (not shown) which is laid against Velcro patch 46 sewn to pelvic apron 34. The opposing side of strap 52 is also provided with a Velcro patch 54, which in the illustrated embodiment is comprised of the hard Velcro hooks. Strap 52 is laid on and connected to pelvic apron 34 and the hip strap 42 in such a manner that it would lie approximately colinearly with the line of portion 40 of apron 34 and with strap 42, if they were laid out on a flat surface as shown in FIG. 6.

As shown in FIGS. 3 and 4, strap 52 is extended between the patient's legs, around the back of the leg, underneath the buttock, against the back of the leg and back to the attachment location on portion 40 close to or actually overlapping pellet 24. Groin strap 52 thus has a sewn Velcro patch on its underside on end 56, which patch can be laid across and attached to Velcro patch 54 on the opposing end 58 of groin strap 52. Thus, one end of hip strap 42 and both ends of groin strap 52 join at the same general location on pelvic apron 34 above or in the close proximity of pellet 24.

As will be better understood by turning to the sectional view of FIG. 5, as described below, a nearly unlimited amount of compressive force can be applied to pellet 24 as a result of this configuration.

Groin strap 52 may be removed from the right side of pelvic apron 34 as shown in FIG. 3 and reattached in a similar manner to the left side. More specifically, strap 52 is placed and attached to its Velcro pad to Velcro patch 48 sewn into portion 36 of pelvic apron 34 and laid in a line of direction approximately colinear with the line of portion 36 and hip strap 42 which is connected to the opposing end of pad 48. Groin strap 52 is then drawn between the legs and again across the upper portion of the back leg underneath the buttock to reattach to its opposing end on top of pelvic apron 34 and patch 48. In such a case, pellet 24 would be moved to the left side of pelvic apron 34 or an additional pellet 24 would be inserted therein. Therefore, it is also possible that two such groin straps would be attached and included within the Kurth compression device 30.

Figure 5:
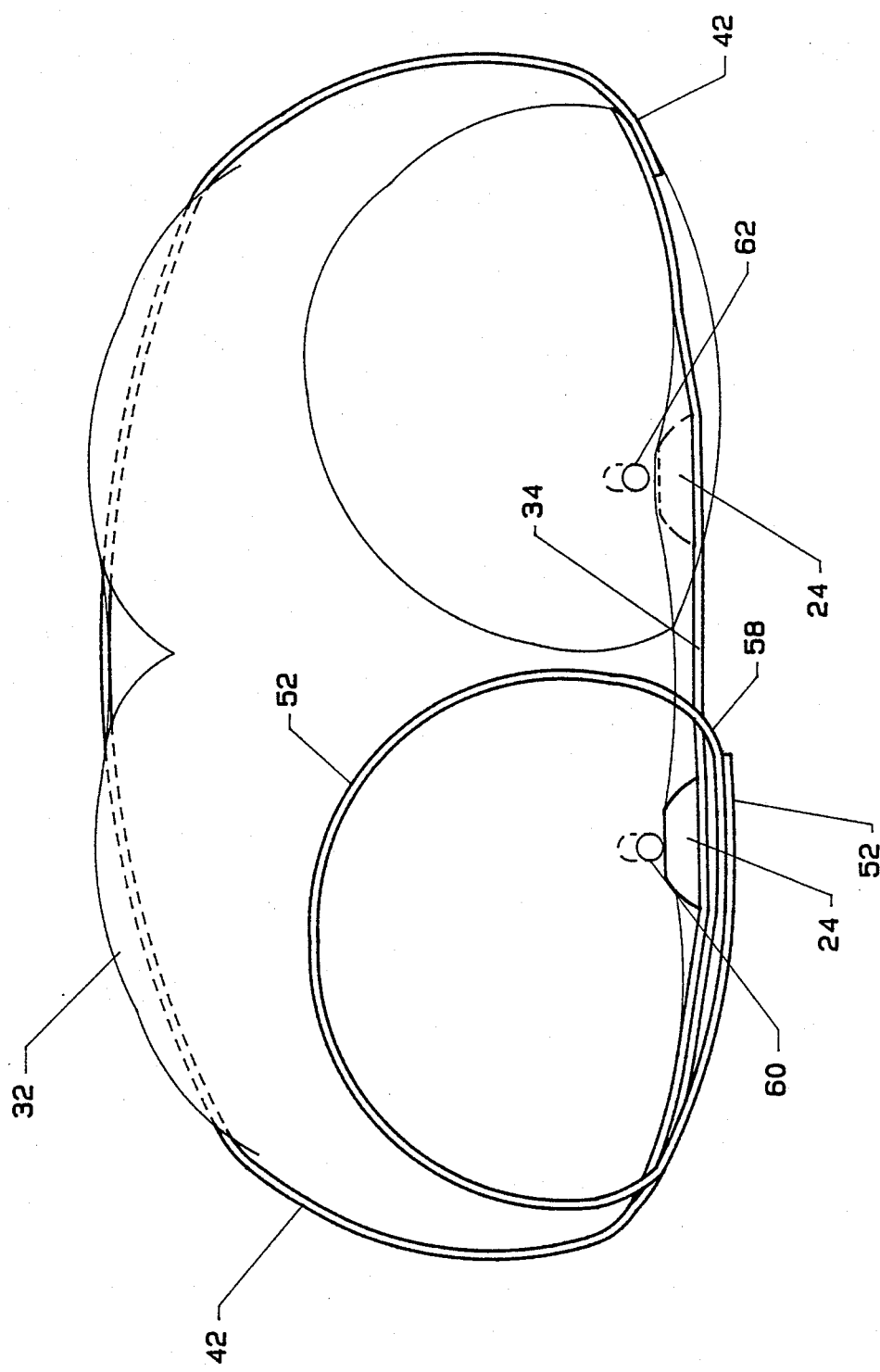
FIG. 5 is a sectional view of the compression device of the invention as would be seen through section lines 5—5 of FIG. 4.

Turn now to FIG. 5 wherein the mechanics of the Kurth compression device 30 may be better understood and depicted. FIG. 5 is an enlarged cross-sectional view of patient 32 as would be seen in a section through lines 5—5 of FIG. 4 looking upwardly. The left femoral artery is denoted by reference numeral 60. Pellet 24 is positioned on the groin immediately above artery 60 and held in place by means of pelvic apron 34. Groin strap 52 then attaches to pelvic apron 34 above pellet 24 and wraps around the leg back across pelvic apron 34 and attaches to the top of opposing end 58 of strap 52. The human body presents a complex shape and the interrelationship of stresses distributed throughout Kurth compression device 30 is similarly complex. It cannot be totally analytically understood with absolute quantified certainty how the physics of device 30 actually distributes tensile forces to result in certain compressive forces. However, it can be graphically seen in FIG. 5 that groin strap 52 may serve as a tourniquet which tightens on the groin where the leg attaches to the hip. It is also believed that a lever action may be achieved which is pivoted on the hip point and concentrated by the relatively sharp curvature of the groin at the femoral arterial site.

Figure 2:
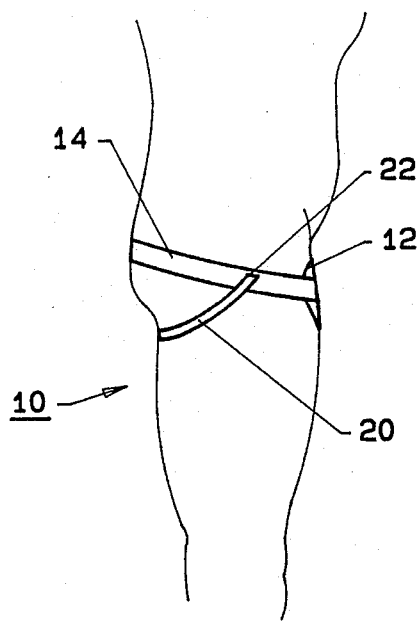
FIG. 2 is a side view of the prior art device depicted in FIG. 1.
Figure 1:
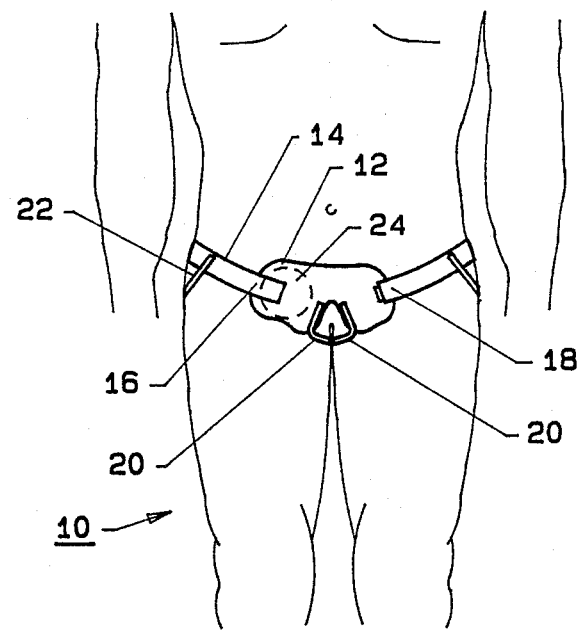
FIG. 1 is a front plan view of a prior art device shown as applied to a patient.

As strap 52 is tightened according to its manual attachment as described above, the amount of compressive force applied to pellet 24 can be varied. The difference in the amount of compressive force which can be applied to pellet 24 by the Kurth compression device 30 as compared to the Colapinto compression device of FIGS. 1 and 2 is substantial and immediately noticeable by patient 32. The compressive force which can be applied by Kurth compression device 30 is sufficient, if desired, to totally close off artery 60. Lesser degrees of force from complete closure to virtually no compressive force can be applied by adjusting the tension on the strap 52.

The sectional view of FIG. 5 also illustrates the aspect of the invention wherein a second pellet 24 is placed over the right femoral artery 62. For the sake of clarity, no groin strap 52 is shown connected to pelvic apron 34 and therefore virtually no compressive force is applied to pellet 34 above femoral artery 62.

Many modifications and alterations may be made by those having ordinary skill in the art without departing from the spirit and scope of the invention. The illustrated embodiment has been set forth only for the purposes of example and should not be taken as limiting the invention which is defined by the following claims.

I claim:

1. An apparatus for applying pressure to an incision point in a femoral vessel within the groin in the abdomen of a human body having a hip point comprising:
   a pellet means for applying a directed force to said femoral vessel of said human body;
   a pelvic apron means for positioning said pellet means over said femoral vessel in one leg, said pellet means attached to said pelvic apron means, said pelvic apron means adapted to encircle said abdomen and including a linear vertically inclined hip strap adapted to extend linearly from said hip point downwardly toward said groin over said incision point in said femoral vessel, said hip strap for exerting a first component of an inward compressive force on said pellet means; and
   groin strap means for applying a second component of said compressive force to said pellet means tending to compress said femoral vessel, so that a substantial inward force is adjustably applied to said femoral vessel and blood flow therefrom is stanched, said groin strap means having a first and second end, said first end colinearly attached to said hip strap, said groin strap means adapted to linearly extend over said point of attachment of said pellet means to said pelvic apron means toward said groin, and adapted to extend around and behind said one leg with said second end of said groin strap means attaching to said pelvic apron means in the overlapping proximity of said point of attachment thereto of said pellet means to include said pellet means within the encirclement of said groin strap means, said groin strap means adapted to encircle the upper portion of said one leg in an oblique plane about said leg and attaching at one point to said said apron means, said groin strap means and pelvic apron means forming in combination a figure of eight with the intersection of said figure of eight at said point of attachment of said pellet means at said groin strap means.

2. The apparatus of claim 1 wherein said pelvic apron means comprises a flexible pelvic apron and a flexible hip strap having two ends, each end attached to said pelvic apron, said hip strap for positioning said pelvic apron on said human body.

3. The apparatus of claim 2 wherein said human body is characterized by having hip points defined by pelvic bones and wherein said hip strap is connected to said pelvic apron over one of said hip points and extends from said hip point toward said groin in a vertically oriented direction more parallel to the length of said human body than not.

4. The apparatus of claim 1 wherein said groin strap is separable from said apparatus has a first and second end and is temporarily and adjustably attached at said first end of said groin strap to said pelvic apron means, and is temporarily and adjustably attached at said second end to said first end of said groin strap, temporary and adjustable attachment of said first end of said groin strap to said pelvic apron means and to its own second end being in the proximity of said pellet means.

5. The apparatus of claim 1 wherein said pelvic apron means comprises a flexible pelvic apron and a flexible hip strap having two ends, each end attached to said pelvic apron, said hip strap for positioning said pelvic apron on said human body, said hip strap being oriented relative to said pelvic apron so that said hip strap extends generally vertically across said abdomen to said groin.

6. The apparatus of claim 5 wherein said pelvic apron means is comprised of a basal portion and at least one inclined portion, said inclined portion having a linear extent lying in a predetermined direction when said pelvic apron is disposed on said human body, said predetermined direction being directed to the hip point and in line with said direction of extension of said groin strap means over said pellet means, said hip strap extending in a colinear direction with said predetermined direction to wrap around the hip point, said hip strap continuing across the back of said human body and over the opposing hip point to be reattached to said pelvic apron, said groin strap being attached to said pelvic apron and lying in a colinear direction with said predetermined direction.

7. The apparatus of claim 6 wherein said groin strap is adjustable to provide variable tension along said groin strap and thus downward compression of said pellet means toward the femoral vessel.

8. A compression device for use as a femoral vascular clotting apparatus for application to an incision point in a femoral vessel in a human pelvis including a pair of opposing hip points, a groin, corresponding legs and corresponding femoral vessels extending through said pelvis into each of said legs comprising:

a shaped mass having a first and second surface, force applied to said first surface being transmitted through said mass to said second surface, said second surface arranged and configured for placement in the proximity of said femoral vessel to apply compressive force to said femoral vessel when said mass is urged into said pelvis against said femoral vessel;

pelvic apron means for securely positioning said shaped mass on said human pelvis, said shaped mass being attachable to said pelvic apron means at a predetermined range of locations between said pelvic apron means and said human pelvis to position said mass proximate to said femoral vessel, said pelvic apron means covering at least a frontal portion of said human pelvis, said pelvic apron means adapted to encircle said human pelvis and including a vertically inclined hip strap adapted to linearly extend from said hip point downwardly toward said groin over said incision point;

linear groin strap means adjustably and colinearly coupled to said hip strap for urging said shaped mass downwardly against said femoral vessel, said groin strap means attached to said hip strap adapted to linearly extend from one of said hip points over said point of attachment of said shaped mass to said pelvic apron means toward said groin, and adapted to extend around and behind said one leg and attaching to said pelvic apron means in the overlapping proximity of said point of attachment thereto of said shaped mass to include said shaped mass within the encirclement of said groin strap means, said groin strap means adapted to encircle said one leg on an oblique plane therethrough where said pelvic apron means encircles said human pelvis to form in combination with said pelvic apron means a figure of eight entwined about said human pelvis and one leg, said shaped mass attachable in the vicinity of the crossing of said figure of eight form, whereby said shaped mass is positioned by said pelvic apron means and whereby said compressive force is transmitted to said first surface of said shaped mass by combination of tension applied by said groin strap means and said hip strap.

9. The compression device of claim 8 wherein said pelvic apron means is positionally fixed with respect to one of said hip points and wherein said groin strap means applies a tensile force across said pelvic apron means to said hip point and through said groin wherein an inwardly compressive force is applied to said first surface of said shaped mass.

10. The compression device of claim 9 wherein said groin strap means is elastically extensible and wherein tensile force applied by said elastically extensible groin strap means is variably adjustable, and wherein said pelvic apron means is comprised of a substantially non-extensible pelvic apron and an elastically extensible hip strap means for binding said pelvic apron to said hip points of said pelvis wherein said pelvic apron means is comprised of a basal portion and at least one inclined portion, said inclined portion having a linear extent lying in a predetermined, vertically inclined direction when said pelvic apron is disposed on said human body, said predetermined vertical inclined direction being directed to the hip point and in line with said direction of extension of said groin strap means over said pellet means, said hip strap means extending in a colinear direction with said predetermined vertical inclined direction to wrap around the hip point, said hip strap means continuing across the back of said human body and over the opposing hip point to be reattached to said pelvic apron, said groin strap being attached to said pelvic apron and lying in a colinear direction with said predetermined vertically inclined direction.

11. A method for applying a compressive force to a femoral vessel within a human pelvis, said pelvis having two opposing hip points, a groin, and one leg extending from said groin, said method comprising the steps of:

stabilizing a shaped mass in position over a selected one of said femoral vessels in said human pelvis by securing a pelvic apron around said human pelvis, said shaped mass being stabilized relative to at least one of said hip points; and applying an inward compressive force into said grion by means of a hip strap attached to said pelvic apron and a groin strap coupled to said shaped mass, said hip strap linearly extending from one of said hip points toward said groin and said groin strap linearly extending from said hip strap to said groin and encircling said one leg and attaching at a point over said shaped mass, said compressive force directed in a direction into said groin, said compressive force being generated by an inward and upward pull by said hip strap in combination with an inward and downward pull by said groin strap, so that said compressive force is applied to said shaped mass and ultimately to said underlying femoral vessel.

12. The method of claim 11 where in step of stabilizing said shaped mass in position, said shaped mass is positioned over said femoral vessel by attachment to a pelvic apron, said pelvic apron being positioned in turn over said human pelvis by means of a hip strap, said hip strap encircling said human pelvis and lying over said opposing points.

13. The method of claim 11 where in said step of applying said compressive force to said pelvic apron, said compressive force is applied to said pelvic apron by means of an extensible elastic groin strap attached at one end to said pelvic apron, extended over said shaped mass, led through said groin, behind said corresponding leg and attached at its opposing end to said pelvic apron in overlapping proximity of said shaped mass.

14. The method of claim 12 where in said step of applying said compressive force to said pelvic apron, said compressive force is applied to said pelvic apron by means of an extensible elastic groin strap attached at one end to said pelvic apron, extended over said shaped mass, led through said groin, behind said corresponding leg and attached at its opposing end to said pelvic apron in overlapping proximity of said shaped mass.

15. An apparatus for applying inward pressure to a puncture site in the inguinal region of a human body having a hip point and groin to stanch blood flow comprising:
   a pellet means for concentrating pressure on said puncture site of said human body;
   a pelvic apron means for positioning said pellet means over said puncture site, said pellet means attached to said pelvic apron means, said pelvic apron means comprising a vertically inclined linear hip strap means for applying an inward compressive force into said groin at least at said puncture site, said hip strap means adapted to linearly extend from said hip point toward said groin; and
   a separable and adjustable groin strap means colinearly connected to said hip strap means to apply a compressive force to said pellet means, so that a substantial inward force is adjustably applied to said puncture site and blood flow therefrom is stanched, said groin strap means colinearly extending with said hip strap means over said point of attachment of said pellet means to said pelvic apron means and adapted to extend toward said groin, around and behind said one leg and attach to itself on said pelvic apron means in the overlapping proximity of said point of attachment thereto of said pellet means to include said pellet means within the encirclement of said groin strap means, said pelvic apron means, hip strap means and groin strap means thus connected with each other to topoligically form a figure-of-eight shape having two loops and a crossing point between said two loops, one loop of said figure-of-eight for encircling the trunk of said human body, the other loop of said figure-of-eight shape for encircling a leg of said human body, and said crossing point of said figure-of-eight for being positioned subtantially over said puncture site a portion of one loop, said crossing point and the contiguous portion of said opposing loop of said figure-of-eight forming a generally straight and generally vertical segment over said pellet means when said apparatus is disposed onto said human body.

16. A method for applying a compressive force to a femoral vessel within a human pelvis, said pelvis having two opposing hip points, a groin, and one leg extending from said groin, said method comprising the steps of:
   stabilizing a shaped mass in position over a selected one of said femoral vessels in said human pelvis, said shaped mass being stabilized relative to at least one of said hip points; and
   providing a linear hip strap adapted to be linearly disposed over a hip arc from one of said hip points toward said groin and over said selected one of said femoral vessels;
   providing a linear groin strap adapted to encircle said leg on an oblique plane, said groin strap attached to said hip strap over said selected one of said femoral vessels, said groin strap colinearly extending with said hip strap to said groin;
   simultaneously tensioning said groin strap on said oblique plane and said hip strap on said hip are to apply an inward compressive force into said groin by means of said hip strap and leg strap by pulling said groin strap around said leg and attaching said groin strap over said shaped mass.

* * * * *